United States Patent
Blanchard et al.

(10) Patent No.: US 12,064,506 B2
(45) Date of Patent: Aug. 20, 2024

(54) COMPOSITION FOR PREVENTING OR REDUCING TRANSEPIDERMAL WATER LOSS AND IMPROVING SKIN BARRIER FUNCTION

(71) Applicant: SOCIETE DES PRODUITS NESTLE S.A., Vevey (CH)

(72) Inventors: Carine Blanchard, Le Mont-sur-Lausanne (CH); Sebastien Holvoet, Montpreveyres (CH)

(73) Assignee: Societe des Produits Nestle S.A., Vevey (CH)

( * ) Notice: Subject to any disclaimer, the term of this patent is extended or adjusted under 35 U.S.C. 154(b) by 364 days.

(21) Appl. No.: 17/415,036

(22) PCT Filed: Dec. 18, 2019

(86) PCT No.: PCT/EP2019/085831
§ 371 (c)(1),
(2) Date: Jun. 17, 2021

(87) PCT Pub. No.: WO2020/127409
PCT Pub. Date: Jun. 25, 2020

(65) Prior Publication Data
US 2022/0062161 A1 Mar. 3, 2022

(30) Foreign Application Priority Data

Dec. 19, 2018 (EP) .................................. 18213823
May 14, 2019 (EP) .................................. 19174260

(51) Int. Cl.
*A61K 8/98* (2006.01)
*A61Q 17/00* (2006.01)
*A61Q 19/00* (2006.01)
*A61Q 19/08* (2006.01)

(52) U.S. Cl.
CPC .............. *A61K 8/986* (2013.01); *A61Q 17/00* (2013.01); *A61Q 19/007* (2013.01); *A61Q 19/08* (2013.01); *A61K 2800/92* (2013.01)

(58) Field of Classification Search
CPC .................................. A61K 8/986; A23J 1/205
See application file for complete search history.

(56) References Cited

U.S. PATENT DOCUMENTS

| | | | | |
|---|---|---|---|---|
| 2011/0021428 A1* | 1/2011 | Mercenier | ............ | A61K 38/018 |
| | | | | 514/8.9 |
| 2014/0044830 A1* | 2/2014 | Mace | ...................... | A23L 33/18 |
| | | | | 426/2 |

FOREIGN PATENT DOCUMENTS

| | | | | |
|---|---|---|---|---|
| EP | 0322589 | 7/1989 | | |
| EP | 2465508 | 6/2012 | | |
| EP | 2684558 | 1/2014 | | |
| FR | 2446634 | 8/1980 | | |
| KR | 20150055666 | 5/2015 | | |
| WO | 2006000350 | 1/2006 | | |
| WO | WO-2008088472 A2 * | 7/2008 | ............ | A23C 21/02 |
| WO | 2017129643 | 8/2017 | | |

OTHER PUBLICATIONS

Shimizu et al. "Dietary Whey Protein Hydrolysate Suppresses Development of Atopic Dermatitis-like Skin Lesions Induced by Mite Antigen in NC/Nga Mice" Allergology International, 2006, vol. 55, pp. 185-189.
Alexander et al. "Partially Hydrolyzed 100% Whey Protein Infant Formula and Reduced Risk of Atopic Dermatitis: A Meta-analysis" JPGN, Apr. 2010, vol. 50, No. 4, pp. 422-430.
Sauser et al. "Partially Hydrolyzed Whey Infant Formula: Literature Review on Effects on Growth and the Risk of Developing Atopic Dermatitis in Infants from the General Population" International Archive of Allergy and Immunology, 2018, vol. 177, pp. 123-134.
Szajewska et al. "A partially hydrolyzed 100% whey formula and the risk of eczema and any allergy: an updated meta-analysis" World Allergy Organization Journal, 2017, vol. 10, No. 27, 11 pages.
Von Berg et al. "Certain hydrolyzed formulas reduce the incidence of atopic dermatitis but not that of asthma: Three-year results of the German Infant Nutritional Intervention Study" J Allergy Clin Immunol, 2007, vol. 119, pp. 718-725.

* cited by examiner

*Primary Examiner* — Qiuwen Mi
(74) *Attorney, Agent, or Firm* — K&L Gates LLP

(57) ABSTRACT

The present invention relates to the use of a milk whey protein hydrolysate for preventing or treating transepidermal water loss (TEWL) and/or TEWL-associated disorders or/and enhancing skin barrier function in young and adult mammals. The protein hydrolysate may be used in the prevention or treatment of TEWL-associated disorders, such as atopic dermatitis, dry or reactive skin or skin dehydration. It may also be used in the cosmetic use of improving skin appearance.

17 Claims, 4 Drawing Sheets

A

B

COMPOSITION FOR PREVENTING OR REDUCING TRANSEPIDERMAL WATER LOSS AND IMPROVING SKIN BARRIER FUNCTION

CROSS REFERENCE TO RELATED APPLICATIONS

The present application is a National Stage of International Application No. PCT/EP2019/085831, filed on Dec. 18, 2019, which claims priority to European Patent Application No. 18213823.0, filed on Dec. 19, 2018, and European Patent Application No. 19174260.0, filed on May 14, 2019, the entire contents of which are being incorporated herein by reference.

TECHNICAL FIELD

The present invention relates to the use of a milk whey protein hydrolysate for preventing or treating transepidermal water loss (TEWL) and/or TEWL-associated disorders or/and enhancing skin barrier function in young and adult mammals.

BACKGROUND OF THE INVENTION

The primary function of the skin is to protect the body against environmental stresses and to prevent against dehydration.

Transepidermal water loss (TEWL) is a term used in dermatology to characterize the loss of water that passes from the inside of a body through the epidermal layer (skin) to the surrounding atmosphere via diffusion and evaporation processes.

Measurement of TEWL is thus a way to measure loss of water through the epidermal layer (skin) and is considered as one of the best markers for skin barrier function and consequently, for the risk of developing a skin associated disease, or disorder, such as dry or scaly skin, seborrheic dermatitis (cradle cap), atopic dermatitis and/or reactive skin (like winter rashes), contact dermatitis, psoriasis, and a range of inflammatory skin conditions such as rosacea, contact dermatitis, perioral dermatitis, nappy rash and perianal dermatitis (especially in infants).

Indeed, an increased TEWL at 2 days and 2 months in infant has shown to be predictive for occurrence of eczema (also known as atopic dermatitis (or AD) at 1 year of age. [Kelleher, M., et al. (2014) "Skin barrier dysfunction measured by transepidermal water loss at 2 days and 2 months predates and predicts atopic dermatitis at 1 year", J Allergy Clin Immunol., April; 135(4):930-5]. The enhancement of skin barrier function from birth to 6 months significantly decreases (50%) the risk of developing eczema (Simpson, E. L. et al. Emollient enhancement of the skin barrier from birth offers effective atopic dermatitis prevention (2014) J. Allergy Clin. Immunol. October, 134(4):818-23).

Therefore, TEWL measurement can also be used to assess and quantify the clinical outcome of a skin disease. TEWL is also a reliable physiological readout to assess compromised skin barrier function as it is well established that an impaired skin barrier eventually leads to loss of water throughout the skin.

TEWL can have genetic and/or environmental etiology. Specifically, it can be the result of a genetic polymorphism leading to a decrease in protective protein expression and thus compromised skin barrier. Skin inflammation, mainly caused by external irritants, can also lead to water loss. Both genetic and environmental components can, together or separately, lead to excessive transepidermal water loss and ultimately trigger different TEWL-associated skin diseases that range from dry skin to more severe conditions such as eczema.

TEWL having a genetic component can lead to dry skin or reactive skin or eczema. Otherwise, the TEWL may be linked to an environmental component, for example, exposure to an irritant through the skin, that then leads to the skin disorder. In certain cases, like in the case of eczema, the development of the skin disorder, may be accompanied by allergic sensitization. In addition to inflammatory skin conditions and dry skin associated skin conditions, increased TEWL is also observed in skin that has been subject to aging, injury- and infection and burns.

For subjects with a genetic predisposition to a reactive skin disorder like eczema (for example subjects with polymorphism in genes such as filaggrin gene or SPINK5), irritants such as soap, transpiration, wool, stress and cold weather may cause skin irritation.

In TEWL-associated disorders, the normal water loss rate is increased due to a diminished barrier function of the epidermis. A TEWL-associated disorder is thus mainly characterized by the symptoms of a dehydrated epidermis like dry or scaly skin. In humans, TEWL associated disorders are often associated with atopic dermatitis and/or reactive skin (like winter rashes). TEWL associated disorders also include psoriasis, seborrheic dermatitis (also known as cradle cap) and a range of inflammatory skin conditions such as rosacea and perioral dermatitis, contact dermatitis, diaper rash and perianal dermatitis (especially in infants).

Current approaches to the prevention and treatment of skin barrier dysfunction related pathologies have focused to date on the administration of skin lipid or skin protein components to the skin. For example, topical application of amphiphilic polymer of lipid/peptide/polysaccharide conjugate derived from chitin has been shown to suppress skin barrier disruption (measured by TEWL) induced from n-hexadecane or oleic acid treatment [SEKI, T., et al., (2015) Development of an Amphiphilic Chitin Derivative with Lipid/Peptide-Type Side Chains Having Skin Protective Ability. J. Nutr. Health Food Eng. 2(3): 00053. DOI: 10.15406/jnhfe.2015.02.00053].

It is, therefore, the object of the present invention to provide compositions for use in the prevention or treatment of transepidermal water loss and/or TEWL-associated disorders and/or to enhance the skin barrier function in mammals.

It is therefore an object of the present invention to provide compositions suitable for administration to humans, including adults, children, toddlers and infants that decrease TEWL and/or improve skin barrier function. The preferred subject group is young humans, especially infants and toddlers.

It is also an object of the present invention to provide compositions suitable for use in improving skin hydration.

SUMMARY OF THE INVENTION

It is the object of the invention to provide new and alternative solutions to the problem of preventing or treating transepidermal water loss and/or TEWL-associated disorders and/or enhancing skin barrier function of infants. The Applicant has developed an animal model to evaluate the effect of compositions on skin barrier function. The results of the experiments surprisingly demonstrate that the administration of a partially hydrolyzed whey protein composition improves barrier function and prevents transepidermal water loss in both adult and neonate mice. The inventors have shown that the hydrolysate in the pure form and also when administered as part of an infant formula was able to improve skin barrier function. Therefore, the hydrolysate, or a composition comprising the hydrolysate, can improve barrier function in young and adult mammals. Generally, administration of the hydrolysate, or of a composition comprising the hydrolysate, to the young or adult mammal may be used to:

prevent or treat TEWL-associated disorders such as ichthyosis vulgaris, diaper rash, dry or scaly skin, seborrheic dermatitis (cradle cap), atopic dermatitis (eczema) and/or reactive skin (like winter rashes), skin inflammatory conditions including psoriasis, contact dermatitis, rosacea and perioral dermatitis and perianal dermatitis (the latter being especially prevalent in infants), treat TEWL caused by skin aging, skin injury and/or burns, improve skin hydration, thus, preventing or treat skin dehydration.

According to one embodiment of the invention, the milk whey partial protein hydrolysate may be used in the prevention or treatment of ichthyosis vulgaris, diaper rash, dry or scaly skin, seborrheic dermatitis, and/or reactive skin (like winter rashes), psoriasis and rosacea in young or adult mammals.

The evaluation of the usefulness of the hydrolysate and compositions containing it, for the treatment or prevention of TEWL and/or TEWL associated disorders, and for enhancing skin barrier function was carried out in a mouse model.

The effect of a partially hydrolysed milk infant formula (pHF), NAN-HA™, also known as BEBA-HA™ or Gerber® Good Start® from Nestle was tested in the animal model experiment described in Example 1 below. This infant formula (pHIF) is a whey-based hypoallergenic partially hydrolyzed formula produced using a two-step hydrolysis process described in European patent application EP0322589. A cow's milk whey hydrolysate suitable for use according to the invention is also present in the infant formula S26-HA™ available from Wyeth. An intact, non-hydrolysed whey-based infant formula (IF), BEBA OPTIPRO1™ from Nestle was also tested, as was the isolated protein hydrolysate (Hydrolysate) and the lipid Blend (lipid Blend) from the pHIF, BEBA-HA™.

Surprisingly, the inventors found that the lipid component of the formula did not have a significant effect on TEWL, but that the protein hydrolysate component did significantly improving skin hydration by reducing TEWL. The inventors further confirmed that hydrolysate regulated Aquaporin 3 gene expression in mouse skin. Increased expression of the latter gene is associated with skin barrier dysfunction.

Thus, the hydrolysate of the current invention has now been shown by the Applicant to improve skin hydration by enhancing the skin barrier function.

Thus, the invention concerns a milk whey partial protein hydrolysate for use in preventing and/or treating TEWL and/or TEWL-associated disorders and/or for use in enhancing skin barrier function or skin hydration in a young or adult mammals. According to one embodiment of the invention, the milk whey partial protein hydrolysate is administered to a human infant, toddler, younger child, older child or adult.

Generally, the milk used to obtain the whey hydrolysate, may be from any animal producing milk whey protein, preferably, cow, goat, sheep, camel or buffalo. Mixtures of milk whey protein animal sources may be used also. Typically, the whey protein hydrolysate is from a cow.

According to one embodiment of the invention, the milk whey partial protein hydrolysate has a NPN/TN % in the range 75%-85%.

According to an embodiment of the invention, administration of the milk whey partial protein hydrolysate may be orally, typically, at a dose of between 0.01-3.0 g/per kg bodymass/day, preferably from 0.5-2 g/per kg bodymass/day.

According to an embodiment of the invention, administration of the milk whey partial protein hydrolysate may be topically, typically, at a dose of from about 0.005% w/w to about 5% w/w, preferably from about 0.05% to 4% w/w, more preferably about 2% w/w.

According to one embodiment of the invention, the milk whey partial protein hydrolysate may be administered to companion animals, preferably cats or dogs.

According to one embodiment of the invention, the milk whey partial protein hydrolysate may be administered, in its pure form or diluted in water or human breast milk, or added to, or contained in a composition that is a nutritional supplement, a human milk fortifier, or an infant formula, starter infant formula, or a follow-up infant formula or a growing up milk.

According to one embodiment of the invention, the milk whey partial protein hydrolysate is used non therapeutically for improving skin hydration in young or adult mammals. Generally, the improvement of skin hydration may be associated with at least one of preventing or reducing skin redness, preventing or reducing skin dryness or flakiness, enhancing the youthful appearance of the skin, enhancing skin firmness, preventing or reducing the appearance of fine lines, preventing or reducing the severity of a dull complexion, increasing the appearance of glow in the skin.

Nutritional intervention was performed all along the experiment with either intact infant formula (IF), partially hydrolysed Infant formula (pHF), protein hydrolysate (Hydrolysate) or with the lipid fraction (Lipid Blend) of the pHF.

Figure 2:
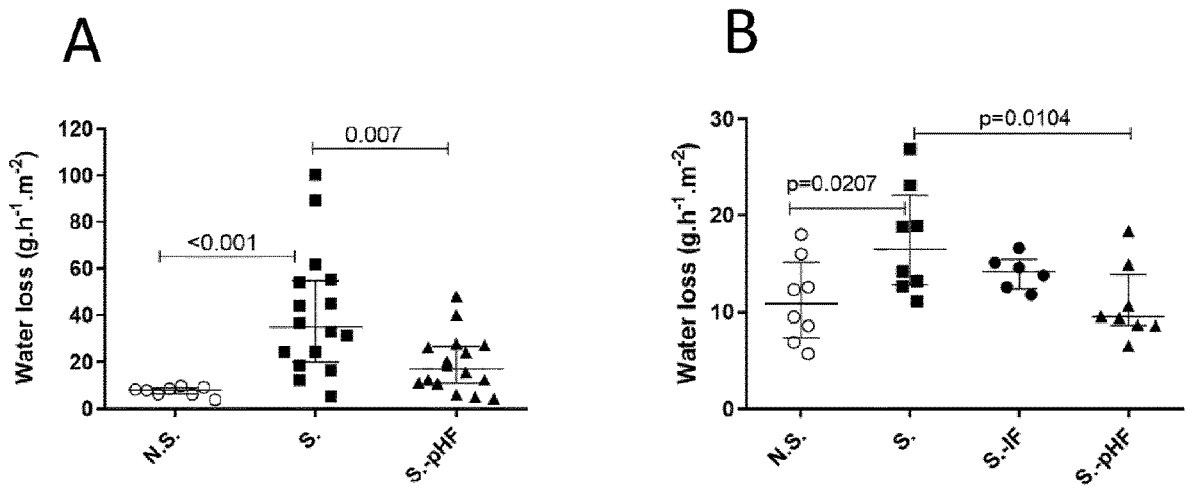

FIG. 2: Effect of pHF and IF on TEWL

TEWL was measured at day 14 in adult mice (A) and at day 30 for neonate (B). Data are expressed as median±SE median. For adult mice, experiment n=8 for non-sensitized (N.S.; empty circle) and n=16 for sensitized (S.; black square) and pHF (S.-pHF; black triangle) groups. Neonate mice experiment n=8 for N.S. and S. groups, n=6 for S.-IF (black circle) and n=8 for S.-pHF.

Figure 3:
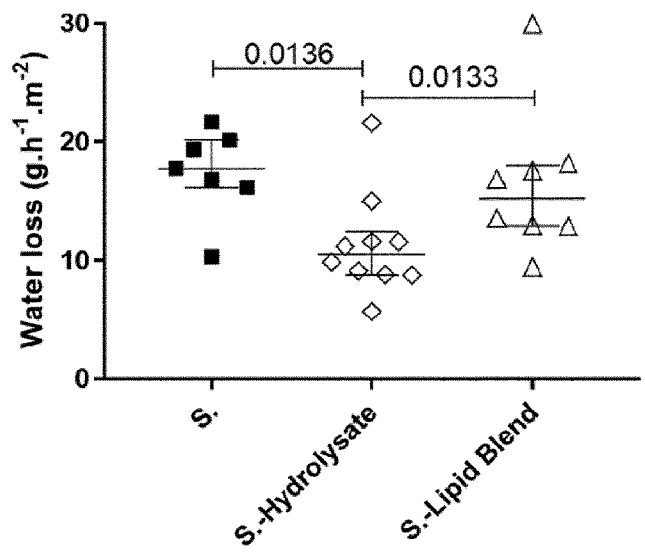

FIG. 3: Effect of supplementation with hydrolysate and lipid blend on TEWL in Af and BLG sensitized neonate models Sensitized animals received Hydrolysate (empty diamond) and Lipid Blend (empty triangle) from birth to day 32. TEWL was assessed at day 30 and quantified. Data are expressed as median±interquartile ranges. N=7 for S., n=10 for S.-Hydrolysate and n=8 for S.-Lipid Blend.

Figure 4:
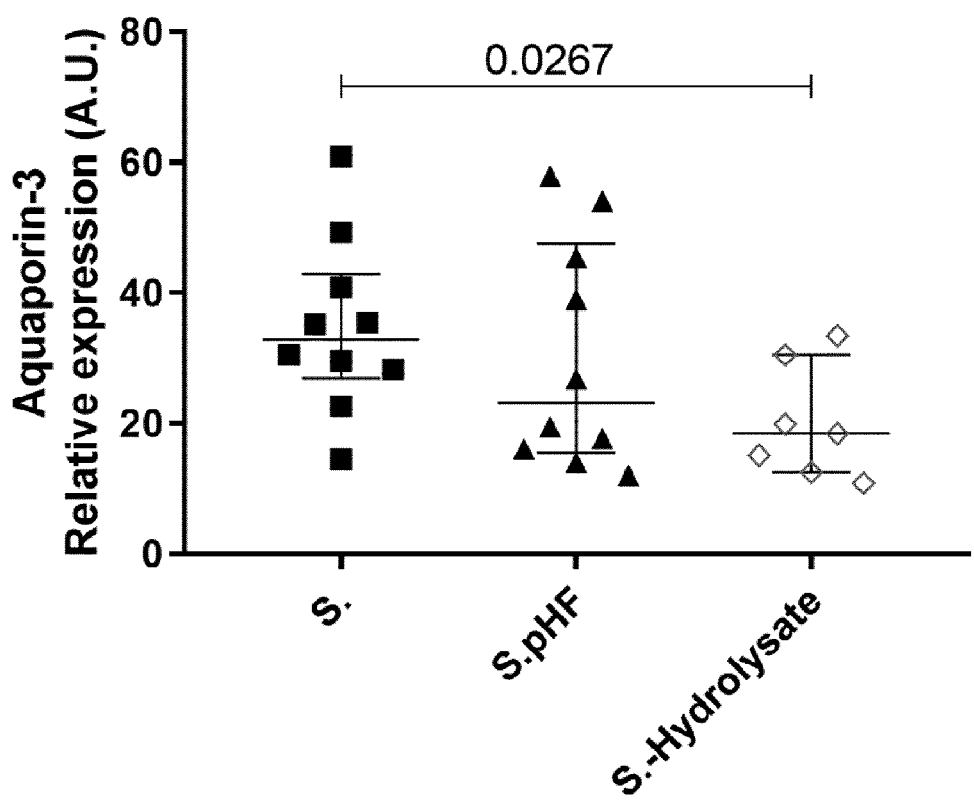

FIG. 4. Effect of supplementation with IF, pHF, hydrolysate on skin barrier function Mouse Aquaporin 3 gene expression in mouse skin Mouse Aquaporin 3 gene expression was measured on the skin patch. Data are expressed in median±interquartile range with n=8 for non-sensitized (N.S.), n=8 for sensitized (S.), n=8 for Intact Formula group (S.-IF), n=7 for partially Hydrolyzed Formula (S.-pHF).

Figure 5:
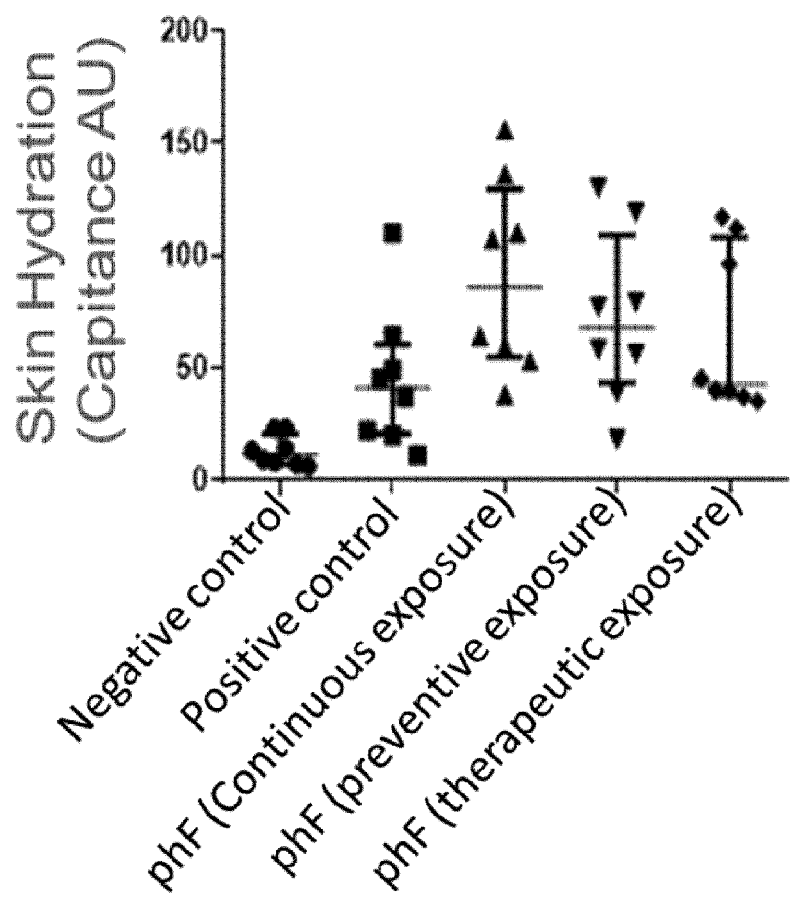

FIG. 5. Effect of supplementation with pHF, on skin hydration as measured by skin capitance.

Mouse skin hydration was measured as skin capitance in mice subjected to an atopic dermatitis model. Data are expressed in median±interquartile range with n=8 for negative control (non sensitized), n=8 for positive control sensitized and supplemented with water, n=8 for mouse supplemented with partially hydrolyzed formula provided either as a preventive strategy (before the second patch), all along the model or only as therapeutic option (during and after the second patch).

DETAILED DESCRIPTION

Any reference to prior art documents in this specification is not to be considered an admission that such prior art is widely known or forms part of the common general knowledge in the field.

As used in this specification, the words "comprises", "comprising", and similar words, are not to be interpreted in an exclusive or exhaustive sense. In other words, they are intended to mean "including, but not limited to.

The term "infant" indicates a child under the age of 18 months.

The term "toddler" indicates a child from about the age of 18 months to 36 months.

The term "young child" indicates a child from about the age of 3 years to 6 years.

The term "older child" indicates a child from about the age of 7 years to 18 years.

"Transepidermal water loss (TEWL)" is defined as the quantity of water that passes from inside a body (animal or plant) through the epidermal layer (skin) to the surrounding atmosphere via diffusion and evaporation processes. Symptoms of TEWL are, in particular, a dry, and/or red, and/or lichenified, and/or itchy, and/or bumpy and/or a scaly skin.

"Transepidermal water loss (TEWL) measurement" according to the present invention means measurement of TEWL in an individual. TEWL measurements are of great importance in evaluating barrier functionality of the epidermal layer. Normal rates of TEWL are compromised due to injury, infection and/or severe damage as in the case of burns. Damage to the stratum corneum and superficial skin layers not only results in physical vulnerability, but also results in an excess rate of water loss. Normal rates of TEWL in human adult forearm are $7\pm3$ $g \cdot h^{-1} \cdot m^{-2}$. In newborn TEWL is higher due to immaturity of the skin. In the sense of the invention, rates of TEWL of 3 $g \cdot h^{-1} \cdot m^{-2}$ above control matched population are considered to be abnormal and indicative of a disorder of the skin (i.e., the epidermal layer).

"TEWL-associated disorders" are the skin conditions in which TEWL is abnormally increased. These include but are not limited to: dry or scaly skin, eczema/atopic dermatitis, seborrheic dermatitis, ichthyosis vulgaris, reactive skin (like winter rashes), psoriasis, dermatitis, rosacea, diaper rashes and idiopathic skin inflammation, skin inflammatory conditions and aging skin. Increased TEWL may also result from skin injury, infection and burns to the skin. Damage to the stratum corneum and superficial skin layers not only results in physical vulnerability, but also results in an excess rate of water loss. Therefore, dehydration, metabolic acidosis, and conditions such as anhydremia or concentration of the blood are often critical issues for healthcare providers to consider in the treatment of burn patients. TEWL associated disorders also include contact dermatitis, rosacea and perioral dermatitis and perianal dermatitis (the latter being especially prevalent in infants). TEWL has been shown to be increased in premature or low birthweight infants, especially in the diaper area. Thus, premature infants are more vulnerable to TEWL-associated disorders.

The etiology of these conditions can be associated with genetic polymorphism leading to the decreased expression of protein highly involved in the skin barrier function such as protein encoded by genes of the epidermal differentiation complex (e.g., filaggrin, involuccrin, sprr) and protein involved in tight junctions. Therefore, the invention relates to the prevention or treatment of skin disorders including eczema or reactive skin or the symptoms caused by reactive skin, burns, psoriasis, dermatitis, rosacea and idiopathic skin inflammation, dry skin or scaly skin.

"Barrier function" or "skin barrier protection" or "skin barrier function" is the function of the (epidermal) barrier to prevent skin dehydration and to prevent the transition of external and internal agents or molecules through the epidermal layer.

The terms "Eczema" and "atopic dermatitis" (AD) are used interchangeably in the present invention. Eczema is an inflammatory, chronically relapsing, non-contagious and pruritic (itch causing) skin disorder. The skin of a patient with eczema overreacts easily to irritants, food, and environmental irritants and becomes red, flaky and very itchy (becoming a reactive skin). It also becomes vulnerable to surface infections caused by bacteria. The skin on the flexural surfaces of the joints is often affected in human subjects. Symptoms may vary from person to person but they are usually present as a red, inflamed, and itchy rash and can quickly develop into raised and painful bumps. The skin tends to be more sensitive and may thicken, crack, become dry or scale. Epidermal barrier dysfunction is considered to be an explanation on the physiopathology of atopic dermatitis. Changes in certain genes encoding structural proteins, epidermal proteases and protease inhibitors predispose to a defective epidermal barrier and increase the risk of developing atopic dermatitis. The strong association between both genetic barrier defects and environmental insults to the barrier with atopic dermatitis suggests that epidermal barrier dysfunction is a primary event in the development of this disease.

An important indicator of barrier function is TEWL. In the current invention, it is assumed that TEWL can be reduced by the administration of the protein hydrolysate to the subjects to be treated, thereby preventing or treating pathologies associated with TEWL. Thus, burn-associated TEWL, psoriasis, perioral and perianal dermatitis, rosacea, diaper rash, seborrheic dermatitis and idiopathic skin inflammation, dry skin or scaly skin as well as eczema, can be treated. TEWL may be prevented or treated in premature or low birthweight infants. Without being bound to any theory, we believe that the effect may be mediated by improving the tight junction system of the skin.

For the purposes of this invention, the terms "treating" or "treatment" mean to decrease or alleviate the symptoms suffered by a mammal, in particular an animal or human being, especially the symptoms of a skin disorder and/or assist in the management of a skin disorder. The terms "treatment" and "treating" further mean to promote or aid recovery of the skin for example to improve the appearance and condition of the skin.

The terms "prevention" or "preventing" mean to stop the onset of symptoms or to reduce the severity of such symptoms suffered by a mammal, in particular an animal or human being. In addition, the terms "prevention" or "preventing" mean to delay the onset of symptoms.

As used herein the terms "enhancing the skin barrier function" or "improving the skin barrier function" mean that the barrier function of the skin is strengthened. This skin barrier function is assessed by measuring transepidermal water loss in dermatology clinics. "Enhancing the skin barrier function" or "improving the skin barrier function" thus decreases the transition of internal or external agents or molecules through the epidermal layer. In particular, this enhancement of barrier function may be mediated by a reduction of the interstitial room between the epidermal cell layers. This may be effected by increasing the number of tight junctions or/and increasing the quality of the tight junctions between the epidermal cells and/or increased expression of protein of the epidermal differentiation complex (such as filaggrin, sprr, NICE, involucrin, loricrin) and/or improving the skin lipid barrier by modulating expression of enzymes involved in skin lipid structures.

As used herein, the term "nutritional composition" includes, but is not limited to, complete nutritional compositions, partial or incomplete nutritional compositions, nutritional supplements, and disease or condition specific nutritional compositions.

The term "nutritional supplement", or "dietary supplement", as used herein, refers to a nutritional product that provides nutrients to an individual that may otherwise not be consumed in sufficient quantities by said individual.

Supplements can for example be provided in the form of a pill, a tablet, a lozenger, a chewy capsule or tablet, a tablet or capsule, or a powder supplement that can for example be dissolved in water or sprinkled on food. Most preferred is a powder supplement that can be dissolved in liquid or sprinkled on food, most preferably dissolved in water. Such supplements typically provide the selected nutrients while not representing a significant portion of the overall nutritional needs of the subject. Typically, they do not represent more than 0.1%, 1%, 5%, 10% or 20% of the daily energy need of the subject.

The term "food product", as used herein, refers to any kind of product that may be safely consumed by a human or animal. Said food product may be in solid, semi-solid or liquid form and may comprise one or more nutrients, foods or nutritional supplements. For instance, the food product may additionally comprise the following nutrients and micronutrients: a source of proteins, a source of lipids, a source of carbohydrates, vitamins and minerals. The composition may also contain anti-oxidants, stabilizers (when provided in solid form) or emulsifiers (when provided in liquid form).

The term "infant formula", as used herein, refers to a composition that is administered to infants and toddlers instead of, or, in addition to human milk. Infant formula (also known as "formula") is defined by the U.S. Federal Food, Drug, and Cosmetic Act (FFDCA) as "a food which purports to be or is represented for special dietary use solely as a food for infants by reason of its simulation of human milk or its suitability as a complete or partial substitute for human milk". Infant formula may contain for example, purified cow's milk whey and casein as a protein source, a blend of vegetable oils as a fat source, lactose as a carbohydrate source, a vitamin-mineral mix, and other ingredients depending on the manufacturer. Infant formulas for infants who are allergic to other cow's milk proteins may contain soybean as a protein source in place of cow's milk, or may include partially or extensively hydrolysed cow's milk protein. Infant formulas may also be based on sheep, goat, camel or buffalo milk. Infant formulas may be especially formulated to meet the nutritional needs of infants in the first six months of life (starter formulas) or from six months onwards (follow-on formulas). Premature or low birthweight infants IF is also available for premature or low birthweight infants.

The term "Growing Up milk" or "GUM" refers to (generally cow's) milk that has been fortified with iron or other minerals and vitamins; it is usually intended for administration to infants from the age of 12 months until they reach about 36 months.

The term "dairy products", as used herein, refers to food products produced from animals such as cows, goats, sheep, yaks, horses, camels, and other mammals. Examples of dairy products are low-fat milk (e.g. 0.1%, 0.5% or 1.5% fat), fat-free milk, milk powder, whole milk, whole milk products, butter, buttermilk, buttermilk products, skim milk, skim milk products, high milk-fat products, condensed milk, crème fraiche, cheese, ice cream and confectionery products, probiotic drinks or probiotic yoghurt type drinks.

The term "pet food product" as used herein refers to a nutritional product that is intended for consumption by pets. A pet, or companion animal, as referenced herein, is to be understood as an animal selected from dogs, cats, birds, fish, rodents such as mice, rats, and guinea pigs, rabbits, etc.

The term "protein hydrolysate" as used herein refers to the product of a protein hydrolysis reaction. Hydrolysates may be characterised as "partial" or "extensive" depending on the degree to which the hydrolysis reaction is carried out. Currently there is no agreed legal/clinical definition of Extensively Hydrolyzed Products. In the current invention, a partial hydrolysate is one in which 60% of the protein/peptide population has a molecular weight of less than 1000 Daltons, whereas an extensive hydrolysate is one in which at least 95% of the protein/peptide population has a molecular weight of less than 1000 Daltons. Hydrolysates may further be characterised by their extent of hyrolysis, or degree of hydrolysis (DH). The DH may be defined as NPN/TN %. NPN/TN % means the Non protein nitrogen divided by the total nitrogen expressed as a percentage. Non-protein nitrogen is amino nitrogen that is free to react with a reagent such as trinitrobenzenesulfonic acid (TNBS). NPN/TN % may be measured as detailed in Adler-Nissen J-, 1979, J. Agric. Food Chem., 27 (6), 1256-1262. In general, extensively hydrolysates are characterised as having a NPN/TN % of greater than 95%, whereas a partially hydrolysed is generally characterized as having a NPN/TN % in the range 70%-90%.

There are currently many examples of casein or whey-based hypoallergenic partially or extensively hydrolyzed formulas currently on the market. For example, NAN-HA™, also known as BEBA-HAT and S26-HA™ from Wyeth are both formulas containing a partial protein hydrolysate; Alfare™ and Altera™, from Nestlé, are examples of formulas containing an extensive protein hydrolysate.

The section headings serve to clarify the subject matter and should not be interpreted to limit the subject matter. If ranges of values are disclosed each individual value is considered to be covered by the range, in particular, each integer number. If not noted otherwise, values in % relate to weight/weight (w/w) values.

It has been surprisingly found that a protein hydrolysate derived from partially hydrolyzed whey protein based infant formula, when administered to young or adult mammals is useful for decreasing transepidermal water loss and/or prevent or treat TEWL-associated disorders and/or for enhancing skin barrier protection.

The animal model used to establish the skin barrier enhancement capability of the hydrolysate of the invention is a murine model of induced epicutaneous sensitization.

This finding was made in a mice model allowing determination of TEWL. The effect was observed in both adult and neonate mice. Therefore, it can be concluded that the milk whey protein hydrolysate can be used in the prevention or treatment of transepidermal water loss, of TEWL-associated disorders, including eczema and/or, in general, for enhancing skin barrier function and increasing skin hydration. Without wanting to be bound to any theory, it is believed that whey protein hydrolysate increases epidermal barrier function by increasing the number or quality of tight junctions in the epidermal cell layer.

Protein Hydrolysate

The hydrolysate of the invention is a partial milk whey protein hydrolysate, i.e., a partial hydrolysate obtained from the hydrolysis of milk whey protein. In a preferred embodiment of the invention, the hydrolysate has an NPN/TN % in the range of 70-90%, preferably 75 to 85%. The latter hydrolysate is a "partial" hydrolysate. This hydrolysate may also be characterised in that 60-70% of its protein/peptide population has a molecular weight of <1000 Daltons. Of course, the exact value may vary depending on the method used for the determination of the extent of hydrolysis.

The protein hydrolysate may be prepared according to enzymatic hydrolysis methods known to the skilled person, as described, for example, in patent application EP0322589 that details a two-step enzymatic hydrolysis method. In a preferred embodiment of the invention, the hydrolysate of the invention is prepared from cow's milk whey protein.

However, it is also possible, according to an embodiment of the invention, to prepare the hydrolysate of the invention from goat, or sheep or buffalo or camel milk whey protein or from a mixture of these whey proteins.

An infant formula containing such a hydrolysate suitable for use in the invention is, for example NAN-HA™, sold by Nestlé and S26-HA™, available from Wyeth.

The hydrolysate composition of the invention generally contains as a source of nitrogen from milk whey proteins, including α-lactalbumin, β-lactoglobulin, bovine serum albumin, casein acid, caseinates, and α, β, κ-casein, for example. The source of nitrogen can provide at least 7 to 25% of the total energy.

In general, the hydrolysate according to the invention may be prepared using the following steps:
  (i) a proteinaceous material containing milk whey protein is hydrolysed so that 60-70% of the protein/peptide population has a molecular weight of <1000 Daltons;
  (ii) then treated to inactivate residual enzyme activity;
  (iii) the whey protein hydrolysate solution may be clarified and subjected to a precipitation treatment or passed onto a chromatography column filled with appropriate resin and the peptidic fractions are recovered.

The proteinaceous material to be treated may be any composition containing milk whey protein material and, in particular, a solution or dispersion of milk whey proteins: whey proteins, acid whey protein, sweet whey proteins, whey protein concentrates, whey protein isolate, demineralized whey powder or caseinates, for example. In general, the protein content may vary within the range of about 70 to 95% by weight.

Typically, the proteinaceous material containing milk whey protein (starting material) is hydrolysed using mixed or purified proteolytic enzymes active in the basic and neutral ranges, for example trypsin, chymotrypsin or pancreatin. The preliminary hydrolysis may be carried out for a relatively short time, preferably 5 to 35 minutes, for example 10 minutes, using a small quantity of enzyme, for example 10% of the total quantity used for the hydrolyses.

In cases where the substrate to be hydrolyzed might tend to coagulate during the heat treatment, a chelating agent, such as calcium or magnesium citrate for example, may be added to the substrate, as indicated, for example, in U.S. Pat. No. 4,748,034. The hydrolysate is then subjected to a treatment to inactivate the enzyme, for example, a heat treatment, for example, at 80° to 100° C. for about 3 to 10 minutes, at a pH value of 6 to 8. In industrial heat exchangers, a temperature of approximately 90° C. and a residence time of the order of 5 minutes have proved to be sufficient.

The hydrolysate may then be cooled to a temperature of about 40° to 60° C. and preferably to a temperature of approximately 55° C., which is the optimal temperature for the hydrolytic activity. The pH value may be preferably adjusted to approximately 7.5 by addition of an aqueous solution of a base. The conditions of the second hydrolysis may vary. For example, it may be carried out discontinuously in batches in a thermostatically controlled tank reactor. After addition of the proteolytic enzyme selected from trypsin, chymotrypsin, pancreatin or a mixture of trypsin and chymotrypsin in aqueous solution, the hydrolysis is carried out for 60 to 180 minutes.

Alternatively, the second hydrolysis may take place continuously for about 1 to 60 minutes, and preferably for 2 to 20 minutes, in a tube which constitutes the turbulent-state reactor. Accordingly, the enzyme should be pumped continuously to the entrance of the dwell tube. The resulting state of high turbulence brings about rapid and intense contact between the enzyme and the substrate. Irrespective of the mode employed (batch or continuous) selected for the second hydrolysis, the hydrolysis product typically undergoes a (heat) treatment to inactivate the enzyme. A heat treatment, for example, may comprise preheating the hydrolysate to about 75° C., and keeping it at that temperature (preferably at 75° to 85° C.) for about 5 minutes. This treatment is advantageously followed by a sterilization step, preferably at ultra-high temperature, for example at 125° to 135° C., for 2 to 3 minutes by injection of steam or in a heat exchanger.

The hydrolysate may then be dried, for example by spray drying or by freeze drying for different applications, or may even be subsequently treated. In the latter case, the enzyme may be inactivated during the subsequent treatment.

According to an embodiment of the invention, the hydrolysate may be provided as mixture of synthetic peptides, optionally, mixed with enzymatically produced milk whey hydrolysate.

The Skin Barrier Enhancing Nature of the Hydrolysate Evidenced In Vivo

The ability of the partial protein hydrolysate of the invention to enhance the skin barrier function in vivo was assessed in an experimental mouse model of TEWL (see Example 1 and FIGS. 1-4).

Figure 1:
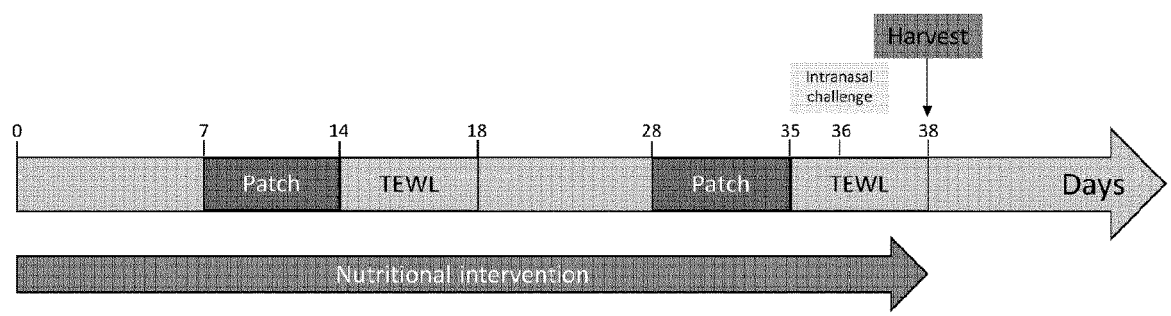
FIG. 1: Atopic dermatitis model in adult and neonate mice and nutritional intervention Adult mice (A) were sensitized by application of two patches containing 200 µg of *Aspergillus fumigatus* (Af) protein extract (sensitized group (S.)) or saline (non-sensitized group (N.S.)) to the shaved back skin of the mice on day 7 to 14 and on day 28 to 35. Mice were all challenged intranasally with 100 µg of Af under isoflurane on day 36. Sacrifice was performed on day 38. Neonate mice (B) were sensitized in the same model but with 3 patches containing 40 ug of Af protein extract on day 10 to 14, 17 to 21 and 24 to 28. Mice were challenged intranasally with 100 µg of Af under isoflurane on day 30. Sacrifice was performed on day 32.
Figure 1:
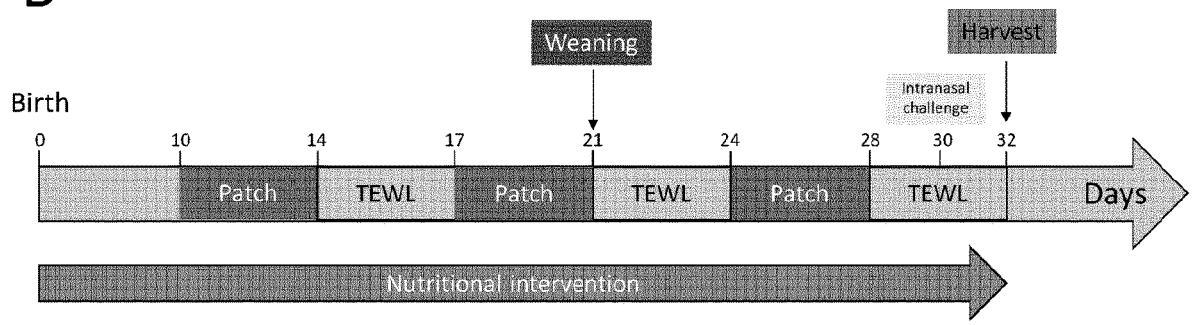

Adult and neonatal mice were epicutaneously sensitized with *Aspergillus fumigatus* (see FIG. 1). Neonatal mice are generally considered a better model for the human situation. For the adult mice, after the first round of sensitization, TEWL was significantly increased in sensitized mice (S.) (34.95 [20.08-55.00] $H_2O$ $g \cdot h^{-1} \cdot m^{-2}$; p<0.001) compared to non-sensitized mice (8.2 [6.45-9.15] $H_2O$ $g \cdot h^{-1} \cdot m^{-2}$) for which the patches were only containing saline (N.S.) (FIG. 2A). A significant decrease in TEWL was observed (17.15 [11.00-27.08] $H_2O$ $g \cdot h^{-1} \cdot m^{-2}$ p=0.007) when pHF was supplemented compared to the sensitized non-supplemented group (S.). This result was transient. After the second patch, the mice developed skin symptoms resembling atopic dermatitis; In the neonatal mice, the TEWL showed significant difference in the S. group compared to the N.S. (10.90 [7.33-15.15] vs 16.50 [12.83-22.05] p=0.0207) only after the third patch. During the experiment, none of the mice developed skin symptoms. pHF significantly reduced TEWL (9.5 [8.63-13.85] p=0.0104) compared to the sensitized mice (not exposed to any formula) (FIG. 2B). Additionally, pHF was also significantly lower than IF, based on area under the curve (data not shown). These data confirm that pHF has a significant beneficial effect on skin barrier function.

Skin Barrier Enhancement Due to Protein Hydrolysate

The inventors have confirmed that the skin barrier enhancing effect is due to the pHF hydrolysate, and not the lipid blend of the pHF.

The lipid and the protein composition are the two main differences between the intact formula (IF) and the pHF. FIG. 3 shows the results of a set of experiments, in which the effect of supplementation with either the hydrolysate or the lipid blend of the pHF on TEWL in neonatal mice was measured. The mice supplemented with the hydrolysate showed significantly lower TEWL measures compared with the S. group (10.53 [8.79-12.43] vs 17.74 [16.15-20.15] p=0.0136) and similar to what was observed with pHF (FIG. 2B). By contrast, the lipid blend did not show any beneficial effect, when compared to the sensitized group, and showed significantly higher TEWL compared to the Hydrolysate group (p=0.0133). These results indicate that the beneficial skin barrier effect observed for pHF is due to the protein hydrolysate component in the formulation, and not the lipid blend. This result is surprising given that, to date, compositions designed to enhance skin barrier function have focused on including components present in skin, like skin associated lipids such as ceramides.

The pHF Hydrolysate Differentially Regulates the Expression of Aquaporin 3 (AQP3)—a Gene Involved in Barrier Function In the experiment detailed in Example 1, Aquaporin 3 (AQP3), known to be associated with TEWL and skin hydration, was significantly decreased in the skin of the neonate mice supplemented with hydrolysate (Hydrolysate) compared to the sensitized mice (S.) (18.4 [±8.7] vs. 32.9 [±13.2]). These results indicate that the protein fraction of the pHF contributes to the protection of the skin by specifically and differentially regulating genes directly involved in skin barrier function.

The pHF Hydrolysate Increase Skin Hydration.

In the experiment detailed in Example 1 and FIG. 5, skin hydration was measure in adult mice in a model of atopic dermatitis. In this model, hydration is increase as a compensation mechanism for TEWL. The supplementation with pHF increase skin hydration in the skin of the mice when supplemented continuously or as a preventive strategy. These results suggest that pHF increase the capacity of the skin to stay hydrated upon challenge.

Therapeutic Uses and Methods

The protein hydrolysate of the invention can be used in the prevention or treatment of transepidermal water loss, and/or prevention or treatment of TEWL-associated disorders, and/or prevention or treatment of a skin disorder characterized by a TEWL that is increased compared to a subject not suffering from the disorder. Additionally, the protein hydrolysate of the invention can enhance the skin barrier function in the young or adult mammal to whom the protein hydrolysate is administered.

In one embodiment of the invention, the protein hydrolysate of the invention can be used for enhancing skin barrier function (i.e. epidermal barrier function) and/or skin hydration. In one embodiment of the invention, the protein hydrolysate can be used for the treatment and/or prevention of eczema or reactive skin. The protein hydrolysate can prevent and/or treat an increase of TEWL. Specifically, the protein hydrolysate can generally prevent an increase of TEWL so that the TEWL value in a subject stays substantially identically or close to the TEWL of a subject not suffering from the disorder.

A normal TEWL measurement in adult human (e.g. forearm) and animals such as rodents is 7±3 $g \cdot h^{-1} \cdot m^{-2}$. Normal values in infants depend on the age of the infant and the maturity of the skin. An abnormal TEWL measurement is defined as 3 $g \cdot h^{-1} \cdot m^{-2}$ above the TEWL measurement of the control population. Thus, reducing a TEWL level that is greater than 10 $g \cdot h^{-1} \cdot m^{-2}$ (e.g. 10.5, 11, 12, 13, 14, 15, 20, 25) by a level of at least 3 $g \cdot h^{-1} \cdot m^{-2}$ is considered to relate to a treatment of a TEWL disorder. In particular, the reduction of a previous TEWL level that was greater than 10 $g \cdot h^{-1} \cdot m^{-2}$ by 2.0, 3.0, 4.0, 5.0 or 10.0 to a value that is closer to or in the range of 7±3 $g \cdot h^{-1} \cdot m^{-2}$ is considered to relate a treatment of TEWL. Preventing a TEWL level from increasing by 3 $g \cdot h^{-1} \cdot m^{-2}$ to a level greater than 10 $g \cdot h^{-1} \cdot m^{-2}$ is considered to relate to the prevention of a TEWL disorder.

The protein hydrolysate of the invention can also be used in a method for therapeutic prevention and/or treatment of a skin disorder characterized by a TEWL which is increased compared to a subject not suffering from the disorder. The disorder to be prevented or treated may be, for example, ichthyosis vulgaris, diaper rash, dry or scaly skin, seborrheic dermatitis, atopic dermatitis and/or reactive skin (like winter rashes), skin inflammatory conditions, psoriasis, contact dermatitis, rosacea, perioral dermatitis and perianal dermatitis (especially in infants).

Therefore, in one embodiment of the invention, the hydrolysate, or a composition comprising it, may be used to prevent or treat at least one of ichthyosis vulgaris, diaper rash, dry or scaly skin, seborrheic dermatitis, atopic dermatitis and/or reactive skin (like winter rashes), skin inflammatory conditions, psoriasis, contact dermatitis, rosacea and perioral dermatitis and perianal dermatitis (especially in infants) in an infant, a toddler or a young child.

In a preferred embodiment of the invention, the hydrolysate, or a composition comprising it, may be used to prevent or treat at least one of diaper rash, seborrheic dermatitis, and dehydrated skin (including dry or scaly skin) in an infant, a toddler, or a young child.

In a preferred embodiment of the invention, the hydrolysate of the invention or a composition comprising it, may be used to improve skin barrier function in an infant, a toddler, or a young child.

In a preferred embodiment of the invention, the hydrolysate of the invention, or a composition comprising it, may be used to increase skin hydration in an infant, a toddler, or a young child.

In an embodiment of the invention, the hydrolysate, or a composition comprising it, may be used to treat burns in an infant, a toddler or a young child.

In one embodiment the hydrolysate, or a composition comprising it, may be used to treat at least one of ichthyosis vulgaris, dry or scaly skin, atopic dermatitis and/or reactive skin (like winter rashes), skin inflammatory conditions, psoriasis, contact dermatitis, rosacea and perioral dermatitis in an older child or an adult.

In a preferred embodiment of the invention, the hydrolysate may be used to treat at least one of rosacea, psoriasis and reactive skin in an older child or an adult.

In an embodiment of the invention, the hydrolysate may be used to treat burns in an older child or an adult.

In a preferred embodiment of the invention, the hydrolysate of the invention may be used to improve skin barrier function in an older child or an adult.

In a preferred embodiment of the invention, the hydrolysate of the invention may be used to increase skin hydration in an older child or an adult.

The protein hydrolysate can be provided in a form that is suitable for topical administration or oral administration and then be administered accordingly. For topical administration, the protein hydrolysate may be formulated in a formulation suitable for topical administration, including semi-solid emulsions, liquid emulsions, gels, creams and milks. The skilled person knows how to formulate such topical formulations.

Oral administration is preferred. The protein hydrolysate may be administered orally directly to the young mammal (including infants and young and older children) or adult mammal alone (pure, or diluted in water or milk, for example) or, as a composition that is an infant milk formula or a food supplement, for example, a human milk fortifier. It may be in the form of a starter infant formula or a follow-on infant formula. It may be in the form of an infant formula for premature or low birthweight infants. It may also be in the form of a Growing up Milk (GUM). It may also be administered in any milk support used during trophic feeding, non-milk based infant formulas, a baby cereal or yoghurt, a baby meal pudding of cheese, a dairy or fruit drink, a smoothy, a snack or biscuit or other bakery item. The hydrolysate may be administered to adults in the form of a drink, food or food supplement.

The hydrolysate may be administered to animals, including companion animals. Thus, the hydrolysate may also be administered in pet food and beverage such as any dry food or kibble, wet food or canned form, or supplement.

The protein hydrolysate may be part of man-made infant formula, man-made hydrolyzed infant formula, or man-made nutritional compositions in general. Such compositions may be embodiments of the invention.

Dosage

According to one embodiment of the invention, the dose of protein hydrolysate is in the range of 0.01 to 3 g/per kg bodymass/day, preferably from 0.1-2 g/per kg bodymass/day. For example, if the protein hydrolysate is administered as part of an infant formula, it may be present in the formula at a concentration of 100 mg/g powder. Typically, the protein hydrolysate will be present about 8-12%, preferably about 10% of the infant formula dry powder. Typically, 13 g of infant formula powder is used to make 100 ml of final liquid formula. A typical dosage of infant formula for an infant of five month-old baby would be three bottles per day of seven (4.3 g) scoops of powder each, and for a six month-old baby or older, two bottles per day of seven (4.3 g) scoops each. The doses are based on an average baby weight for a six-month-old being about 8 kg, and for a twelve-month-old being about 9.5 kilos.

For topical administration, the protein hydrolysate may be present in the topical formulation at a concentration of from about 0.005% w/w to about 5% w/w, preferably from 0.5% to 4% w/w, more preferably 2% w/w.

Administration Period

The period of administration of the protein hydrolysate of the invention can be continuous or discontinuous. Continuous administration is preferred for a more sustained effect. However, it is speculated that a discontinuous pattern (for example, daily administration during one week per month, or during alternate weeks) can nevertheless induce positive effects on the young mammal or adult.

In general, while positive effects are expected with relatively short duration of administration (for example, daily administration during one to four weeks), longer durations are believed to provide enhanced effect (for example, a duration of three to six months in humans, and corresponding periods in other mammals).

In an embodiment of the invention, the protein hydrolysate is intended for consumption by an infant. In this case, consumption may start from birth or from the age of 1, 2, 3, 4, 5, 6, 7, 8, 9, 10, 11 or 12 months or at any age until approximately 18 months.

In an embodiment of the invention, the protein hydrolysate is intended for consumption by a toddler. In this case, consumption may start from approximately 18 months old or any age until the age of approximately 36 months old.

In an embodiment of the invention, the protein hydrolysate is intended for consumption by a young child. In this case, consumption may start from the age of three years old or from the age of 4, or 5, or 6 years old, or any age until the age of approximately 7 years old.

In an embodiment of the invention, the protein hydrolysate is intended for consumption by an older child. In this case, consumption may start from the age of seven years old or from the age of 8, 9, 10, 11, 12, 13, 14, 15, 16, 17, or 18 years old, or any age until 18 years old.

In an embodiment of the invention, the protein hydrolysate is intended for consumption by an adult human. In that case consumption may start at any age from the age of 18 years old. Consumption may continue indefinitely.

Enhancement of the skin barrier function may induce relief from disorders associated with TEWL in the medium term (during the treatment or within 1, 6, 12 or 18 months after the treatment). Alternatively, or additionally, the enhancement of the skin barrier function may induce relief from disorders associated with TEWL later in life (e.g. 24, 36, 48, 72 months after the treatment), especially when the immune system has matured.

Animal, including cats and dogs, often have skin problems including disorders associated with TEWL. Therefore, in another embodiment of the invention, the hydrolysate may be administered to an animal, preferably a cat or a dog. In the case of administration to animals, the appropriate adaptations may be made regarding dosing the hydrolysate as a function of the animal's weight and phenotype.

Administration with Other Compounds

The protein hydrolysate may be administered alone (pure or diluted in water or milk, including human breast milk, for example) or in a mixture with other compounds (such as dietary supplements, nutritional supplements, medicines, carriers, flavors, digestible or non-digestible ingredients).

The protein hydrolysate may be administered, for example, to a young infant, as part of a composition that is a human milk fortifier, or other nutritional supplement. It may, for example, be administered to an infant, as part of be an infant formula, including a premature or low-birthweight infant formula, or a starter formula, a follow-up formula. It may also be administered as part of a nutritional composition for children with particular physiological/pathological conditions.

If the hydrolysate is to be administered to adults, it may be administered as a part of a food, drink or dietary supplement. The protein hydrolysate may also be administered to all subjects (young mammals or adults alike) in a pharmaceutical composition.

In one embodiment of the invention, the protein hydrolysate may originate, in part or in full, from sweet whey from which the cGMP has been removed. Reference is made in that regard to EP880902 that describes a process that allows the removal of practically all the caseino-glyco-macropeptide (a fraction that is rich in threonine and poor in tryptophan) from bovine whey thereby increasing the alpha-lactalbumin proportion (a fraction very rich in tryptophan). By combining this modified sweet whey fraction with skim milk, and with the addition of some free L-histidine and L-arginine (in order to reach the minimum amounts of these amino acids required by EC Directive), the composition comprising the hydrolysate according to the invention, has an amino acid profile much closer to that of human milk, characterized, in particular, by comparable tryptophan and threonine levels, allowing the adaptation of its protein content to that of human.

Thus, having the above described optimized protein profile, it is understood that the hydrolysate of the invention can deliver both a prevention or treatment of TEWL and TEWL associated disorders, and/or enhance the skin barrier function while providing the optimized protein nutritional value.

The hydrolysate may be administered, for example, as part of an infant formula at a concentration of about 8-12 g/100 g infant formula powder, preferably 10 g/100 g infant formula powder.

The hydrolysate may contain as a source of nitrogen, proteins or peptides, particularly from milk proteins, from cow or goat or sheep, such as whey proteins, alpha-lactalbumin, β-lactoglobulin, bovine serum albumin, casein acid, caseinates, or alpha, beta, kappa-casein, for example. The source of nitrogen can provide at least 7 to 25% of the total energy.

Vitamins and minerals are examples of typical dietary supplements. In a preferred embodiment, the composition is administered together with other compounds that enhance the described effect on the enhanced skin barrier function of the young mammal or adult.

Other potential ingredients that may be added to the composition comprising the hydrolysate of the invention are, for example probiotics and prebiotics.

Non-limiting examples of known probiotic compounds are *Bacillus, Bifidobacterum, Lactobacillus Saccharomyce, Streptococcus thermophilus, E. Faecium, E. Coli Nissle*. In particular, probiotics and non-replicating probiotics, such as the genus *Lactobacillus, Bifidobacterium* or combination thereof, for example *Lactobacillus paracasei, Lactobacillus GG, Lactobacillus rhamnosus, Bifidobacterium longum, Bifidobacterium lactis, Bifidobacterium breve*, or combination thereof, and applications of these bacteria.

Non-limiting examples of known prebiotic compounds are carbohydrate compounds selected from the group consisting of inulin, fructooligosaccharide (FOS), short-chain fructooligosaccharide (short FOS), chain galacto-oligosaccharide (GOS), xylooligosaccharide (XOS), glangliosides, partially hydrolyzed guar gum (PHGG), acacia gum, soybean-gum, or mixtures thereof.

The prebiotics can also be a BMO (bovine's milk oligosaccharide) and/or a HMO (human milk oligosaccharide) such as N-acetylated oligosaccharides, sialylated oligosaccharides, fucosylated oligosaccharides and any mixtures thereof.

A particular example of prebiotic is a mixture of galacto-oligosaccharide(s), N-acetylated oligosaccharide(s) and sialylated oligosaccharide(s) in which the N-acetylated oligosaccharide(s) represent 0.5 to 4.0% of the oligosaccharide mixture, the galacto-oligosaccharide(s) represent 92.0 to 98.5% of the oligosaccharide mixture and the sialylated oligosaccharide(s) represent 1.0 to 4.0% of the oligosaccharide mixture. This mixture is hereinafter referred to as "CMOS-GOS". For example, a composition for use according to the invention can contain from 2.5 to 15.0 wt % CMOS-GOS on a dry matter basis with the proviso that the composition comprises at least 0.02 wt % of an N-acetylated oligosaccharide, at least 2.0 wt % of a galacto-oligosaccharide and at least 0.04 wt % of a sialylated oligosaccharide. WO 2006/087391 and WO 2012/160080 provide some examples of production of CMOS-GOS.

In particular, the human milk oligosaccharides, for example sialylated oligosaccharides, described in WO 2012/069416 published on May 31, 2012 may be included in the composition according to the invention.

In one embodiment the composition comprises a mix of oligosaccharides according to WO 2007/090894 (general teaching and specifically Example 1). It may be in particular used in combination with GOS. The composition may comprise an oligosaccharide mixture which comprises 5-70 wt % of at least one N-acetylated oligosaccharide selected from the group comprising GalNAcα1,3Galβ1,4Glc and Galβ1,6GalNAcα1,3Galβ1,4Glc, 20-90 wt % of at least one neutral oligosaccharide selected from the group comprising Galβ1,6Gal, Galβ1,6Galβ1,4Glc, Galβ1,6Galβ1,6Glc, Galβ1,3Galβ1,3Glc, Galβ1,3Galβ1,4Glc, Galβ1,6Galβ1,6Galβ1,4Glc, Galβ1,6Galβ1,3Galβ1,4Glc Galβ1,3Galβ1,6Galβ1,4Glc and Galβ1,3Galβ1,3Galβ1,4Glc (commercially available under the trademarks Vivinal® and Elix'or) and 5-50 wt % of at least one sialylated oligosaccharide selected from the group comprising NeuAcα2,3Galβ1,4Glc and NeuAcα2,6Galβ1,4Glc.

One or more essential long chain fatty acids (LC-PUFAs) may be included in the composition. Examples of LC-PUFAs that may be added are docosahexaenoic acid (DHA) and arachidonic acid (AA). The LC-PUFAs may be added at concentrations so that they constitute greater than 0.01% of the fatty acids present in the composition.

One or more food grade emulsifiers may be included in the nutritional composition if desired; for example, diacetyl tartaric acid esters of mono- and di-glycerides, lecithin and mono- or di-glycerides or a mixture thereof. Similarly, suitable salts and/or stabilisers may be included. Flavours can be added to the composition.

The protein hydrolysate may be incorporated into or be present in a composition that is an infant "preterm formula" for infants born before term or having a low birth weight, a "starter formula" or a "follow-on formula". An example of such starter formula is given in Example 2.

Non-Therapeutic Uses and Methods

The protein hydrolysate of the invention can be used non-therapeutically in the prevention or treatment of transepidermal water loss, and/or prevention or treatment of TEWL-associated skin states or phenotypes, and/or prevention or treatment of a skin state characterized by a TEWL which is increased compared to a subject not having this skin state, and/or to enhance the skin barrier function, in the young or adult mammals. Generally, the non-therapeutic applications are suitable for older children and adults.

In one embodiment, the protein hydrolysate of the invention can be used non therapeutically for the improvement of skin hydration, including an improvement of the appearance of the skin. The improvement of the appearance of the skin may be observed as any one or more of the following: preventing or reducing skin redness, preventing or reducing skin dryness or flakiness, enhancing the youthful appearance of the skin, enhancing skin firmness, preventing or reducing the appearance of fine lines, preventing or reducing the severity of a dull complexion, increasing the appearance of glow in the skin.

In an embodiment, the protein hydrolysate is intended for consumption by a human subject, for example, an older child. In this case consumption may start from the age of seven years old or from the age of 8, 9, 10, 11, 12, 13, 14, 15, 16, 17, or 18 years old.

In an embodiment, the protein hydrolysate is intended for consumption by a human subject, for example, an adult. In that case consumption may start from the age of 18 years old. Consumption may continue indefinitely.

The invention is further described with reference to the following examples. It will be appreciated that the invention as claimed is not intended to be limited in any way by these examples.

Example 1

FIG. 1 shows a schematic representation of the mouse model.

Atopic Dermatitis Model on Adult Mouse Model

The animal study protocol VD3059 was approved by the Service Vétérinaire du Canton de Vaud', Switzerland. Briefly, 5-week-old female BALB/c mice (BALB/cByJ JAX™ mice strain from Charles River, L'Arbresle, France) were anesthetized under isoflurane (Baxter, Volketswil, Switzerland) at day 7. Skin of the back of the mice was shaved with an electric razor and cleaned with a 70% isopropanol (VWR, Nyon, Switzerland) solution. 100 µl of *Aspergillus fumigatus* (Af) protein extract (Greer Laboratories Lenoir, NC, USA) at 2 mg/ml [sensitized group (S.)] or 100 µl of a 0.9% NaCl solution (Merck; Zoug, Switzerland) [Non Sensitized group (N.S.)] was applied on a 1×1 cm patch of a sterile gauze (Hartmann; Dermaplast, Chatenois, France) and secured on the skin with a bio-occlusive transparent dressing (Systagenix; Bioclusive, San Antonio, Texas, USA, Switzerland) and a Band-Aid (Mefix; Wasquehal, France). Patches were removed at day 14. A second patch was applied under same conditions at day 28 up to day 35. Mice were challenged intranasally under isoflurane anesthesia at day 36 with 100 µg of *Aspergillus* diluted in 0.9% NaCl, and euthanatized at day 38.

Atopic Dermatitis Model on Neonate Mouse Model

The animal study protocol VD2382.1 was approved by the Service Vétérinaire du Canton de Vaud', Switzerland. Briefly, ten days old BALB/cByJ neonate mice, were sensitized via a skin patch on the back of the animal. The patch was applied for a duration of 5 consecutive days before removal. In total, 3 patches were applied with 3 days between each patch. The sensitization was performed under anesthesia. Briefly, the back skin was shaved with an electric razor when needed and skin was cleaned with 70% isopropanol solution. 20 µl (patch-1), 50 µl (patch-2) and 100 µl (patch-3) of *Aspergillus fumigatus* protein extract at 2 mg/ml or Beta-lactoglobulin (BLG) (Sigma Aldrich, Buchs SG, Switzerland) (sensitized S.) or NaCl 0.9% (non-sensitized N.S.) was applied on a 0.3 (patch-1), 0.5 (patch-2) or 1 cm² (patch-3) patch of a sterile gauze and secured on the skin with a bio-occlusive transparent dressing and a Band-Aid. Mice were challenged intranasally under isoflurane anaesthesia at day 30 with 100 µg of Af diluted in 0.9% NaCl and euthanatized at day 32.

Nutritional Intervention

In the adult mouse model, partially hydrolysed formula ((pHF), Beba-HA1, (NWHSB 228, Nestle Switzerland), was given ad libitum from day 0 to day 38 at the concentration of 146 mg/ml. Neonate were fed from first day of life to their $11^{th}$ day with 10 to 20 µl of intact formula ((IF) Beba optipro1, (NWSB003, Nestle, Switzerland) or pHF or Hydrolysate or lipid fraction (Nestle, Bissenhofen, Germany). At weaning pups were separated from mothers and formulas were given ad libitum up to the harvest. Formulas were given in drinking bottle and changed every day. Formula's (IF and pHF) were prepared with manufacture's recommended reconstitution dose. Hydrolysate concentration were based on protein content of IF. The same intervention was used for the lipidic fraction.

Transepidermal Water Loss Measurement

TEWL was measured after patch removal on the patch area with a Tewameter® (TM300; Courage+Khazaka electronic; Cologne, Germany) before and after patch removals on the skin patch area from day 14 to 18 and 35 to 38 in the adult model and from day 14 to 17, day 21 to 24 and 28 to 32 for neonate model.

Skin Hydration

Skin Hydration was measured after patch removal on the patch area with a the Skinlab Combo probe for hydration measurement 35 to 38 in the adult model (FIG. 5).

Example 2

An example of the composition of an infant formula for use according to the present invention is given below. This composition is given by way of illustration only.

| Nutrient | Per 100 kcal | Per litre |
| --- | --- | --- |
| Energy | 100 | 670 |
| Protein hydrolysate* | 1.83 | 12.3 |
| Fat | 5.3 | 35.7 |
| Linoleic acid (g) | 0.79 | 5.3 |
| α-Linolenic acid (mg) | 101 | 675 |
| Lactose (g) | 11.2 | 74.7 |
| Prebiotic (100% GOS) (g) | 0.64 | 4.3 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (µg) | 8 | 50 |
| Se (µg) | 2 | 13 |
| Vitamin A (µg RE) | 105 | 700 |
| Vitamin D (µg) | 1.5 | 10 |

-continued

| Nutrient | Per 100 kcal | Per litre |
|---|---|---|
| Vitamin E (mg TE) | 0.8 | 5.4 |
| Vitamin K1 (µg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (µg) | 9 | 60 |
| Pantothenic acid (mg) | 0.45 | 3 |
| Vitamin B12 (µg) | 0.3 | 2 |
| Biotin (µg) | 2.2 | 15 |
| Choline (mg) | 10 | 67 |
| Fe (mg) | 1.2 | 8 |
| I (µg) | 15 | 100 |
| Cu (mg) | 0.06 | 0.4 |
| Zn (mg) | 0.75 | 5 |
| Lactobacillus GG | $2 \times 10^7$ cfu/g of powder | |

*Protein hydrolysate produced according to the method described in EP0322589

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

The invention claimed is:

1. A method for treating transepidermal water loss (TEWL) and/or a TEWL-associated disorder and/or for enhancing skin barrier function or skin hydration in a young or adult mammal in need thereof, the method comprising:
administering to the young or adult mammal in need thereof a composition comprising a milk whey partial protein hydrolysate, and the composition has a non-protein nitrogen (NPN)/total nitrogen (TN) % of 75%-85%.

2. The method according to claim 1 wherein the milk whey partial protein hydrolysate has a milk origin from an animal selected from the group consisting of cow, goat, sheep, camel, buffalo and a mixture thereof.

3. The method according to claim 1, wherein the composition is an infant formula dry powder, and the milk whey partial protein hydrolysate is 8-12 wt. % of the composition.

4. The method according to claim 1 for treatment of a TEWL-associated disorder selected from the group consisting of ichthyosis vulgaris, diaper rash, dry skin, scaly skin, seborrheic dermatitis, atopic dermatitis, reactive skin, psoriasis, contact dermatitis, rosacea, perioral dermatitis, perianal dermatitis, contact dermatitis, and combinations thereof.

5. The method according to claim 1 for treatment of a TEWL-associated disorder selected from the group consisting of ichthyosis vulgaris, diaper rash, dry skin, scaly skin, seborrheic dermatitis, reactive skin, psoriasis, rosacea, and combinations thereof.

6. The method according to claim 1 for treatment of skin dehydration.

7. The method according to claim 1 wherein the young or adult mammal is a human infant.

8. The method according to claim 1, wherein the milk whey partial protein hydrolysate is administered orally to the young or adult mammal in need thereof.

9. The method according to claim 1, wherein the milk whey partial protein hydrolysate is administered orally at a dose between 0.01-3.0 g/per kg bodymass/day.

10. The method according to claim 1, wherein the mammal is a companion animal.

11. The method according to claim 1, wherein the milk whey partial protein hydrolysate is administered in its pure form or diluted in water or human breast milk.

12. The method according to claim 1, wherein the young or adult mammal is not allergic to cow milk.

13. The method according to claim 1, wherein the milk whey partial protein hydrolysate is from cow.

14. The method according to claim 1, wherein the composition further comprises at least one prebiotic.

15. The method according to claim 1, wherein the composition further comprises at least one probiotic.

16. A method for treatment of TEWL caused by skin aging, skin injury and/or burns in a young or adult mammal in need thereof, the method comprising:
administering to the young or adult mammal in need thereof a composition comprising a milk whey partial protein hydrolysate, and the composition has a non-protein nitrogen (NPN)/total nitrogen (TN) % of 75%-85%.

17. A method for preventing and/or treating transepidermal water loss (TEWL) and/or a TEWL-associated disorder and/or for enhancing skin barrier function or skin hydration in a young or adult mammal in need thereof, the method comprising:
administering to the young or adult mammal in need thereof a composition comprising a milk whey partial protein hydrolysate, and the composition has a non-protein nitrogen (NPN)/total nitrogen (TN) % of 75%-85%,
wherein the milk whey partial protein hydrolysate is administered topically and is about 0.005% w/w to about 5% w/w of the composition.

* * * * *